(12) United States Patent
Wendland et al.

(10) Patent No.: US 10,973,987 B2
(45) Date of Patent: Apr. 13, 2021

(54) DRUG DELIVERY DEVICE

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 61 days.

(21) Appl. No.: 16/316,722

(22) PCT Filed: Jul. 12, 2017

(86) PCT No.: PCT/EP2017/067503
§ 371 (c)(1),
(2) Date: Jan. 10, 2019

(87) PCT Pub. No.: WO2018/011249
PCT Pub. Date: Jan. 18, 2018

(65) Prior Publication Data
US 2019/0240420 A1    Aug. 8, 2019

(30) Foreign Application Priority Data
Jul. 14, 2016 (EP) .................................. 16179488

(51) Int. Cl.
*A61M 5/32* (2006.01)
*A61M 5/24* (2006.01)
*A61M 5/315* (2006.01)

(52) U.S. Cl.
CPC ............ *A61M 5/3202* (2013.01); *A61M 5/24* (2013.01); *A61M 5/31565* (2013.01); *A61M 5/31571* (2013.01); *A61M 5/3213* (2013.01)

(58) Field of Classification Search
CPC .. A61M 5/3202; A61M 5/31565; A61M 5/24; A61M 5/31571; A61M 5/3213
See application file for complete search history.

(56) References Cited

U.S. PATENT DOCUMENTS

2003/0233070 A1    12/2003  de la Serna et al.
2009/0299278 A1*   12/2009  Lesch, Jr. ........... A61M 5/2033
                                                              604/68

(Continued)

FOREIGN PATENT DOCUMENTS

WO       WO 02/17996          3/2002
WO       WO-0217996 A1 *      3/2002  .......... A61M 5/2033

(Continued)

OTHER PUBLICATIONS

International Preliminary Report on Patentability in Application No. PCT/EP2017/067503, dated Jan. 15, 2019, 6 pages.

(Continued)

*Primary Examiner* — Lauren P Farrar
(74) *Attorney, Agent, or Firm* — Fish & Richardson P.C.

(57) ABSTRACT

The present disclosure relates to a drug delivery device, including:
  a body adapted to retain a medicament cartridge,
  a cap attachable to a distal end of the body to cover an opening thereof,
  an activation mechanism arranged within the body,
wherein the cap includes an activation feature adapted to be inserted into an activation opening of the body in order to actuate the activation mechanism or allow actuation thereof.

18 Claims, 5 Drawing Sheets

(56) References Cited

U.S. PATENT DOCUMENTS

| | | | | |
|---|---|---|---|---|
| 2010/0185148 A1* | 7/2010 | Gillespie, III | ...... | A61M 5/2033 604/110 |
| 2011/0046565 A1* | 2/2011 | Radmer | .................. | A61M 5/24 604/211 |
| 2013/0079708 A1 | 3/2013 | Wimpenny et al. | | |

FOREIGN PATENT DOCUMENTS

| WO | WO 2009/092807 | 7/2009 |
|---|---|---|
| WO | WO 2011/145999 | 11/2011 |
| WO | WO 2012/160163 | 11/2012 |
| WO | WO 2014/009705 | 1/2014 |
| WO | WO 2015/185686 | 12/2015 |

OTHER PUBLICATIONS

International Search Report and Written Opinion in Application No. PCT/EP2017/067503, dated Sep. 12, 2017, 10 pages.

* cited by examiner

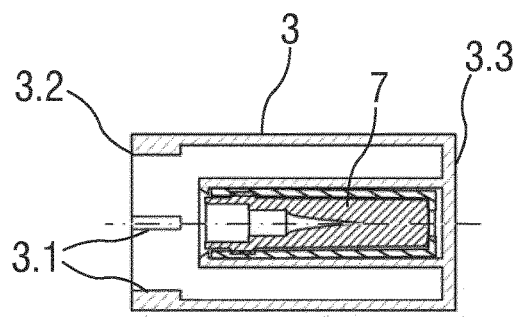
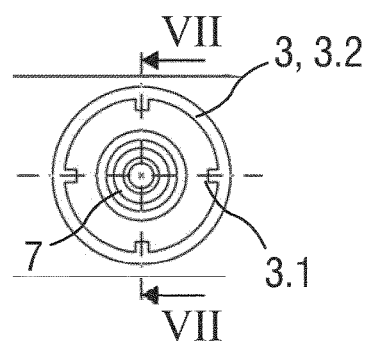
FIG 7  FIG 8
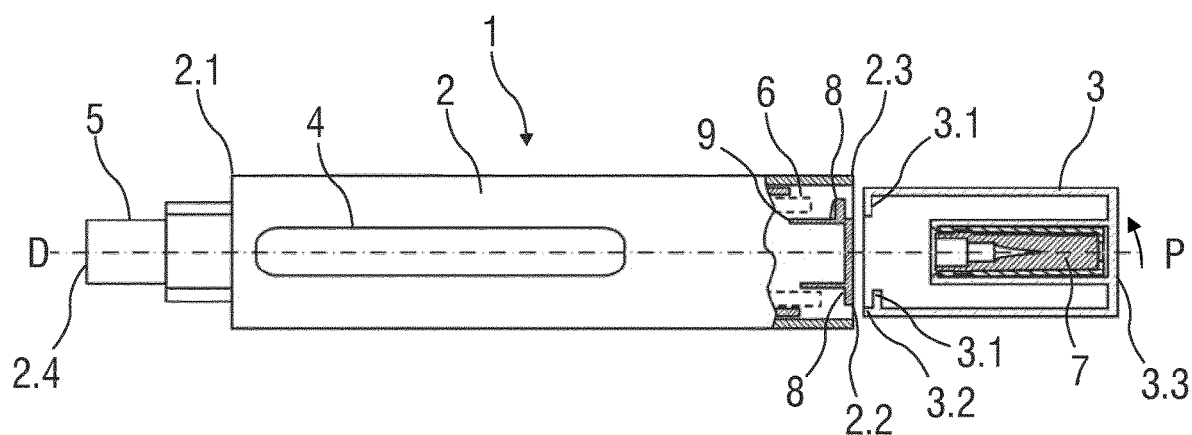
FIG 9
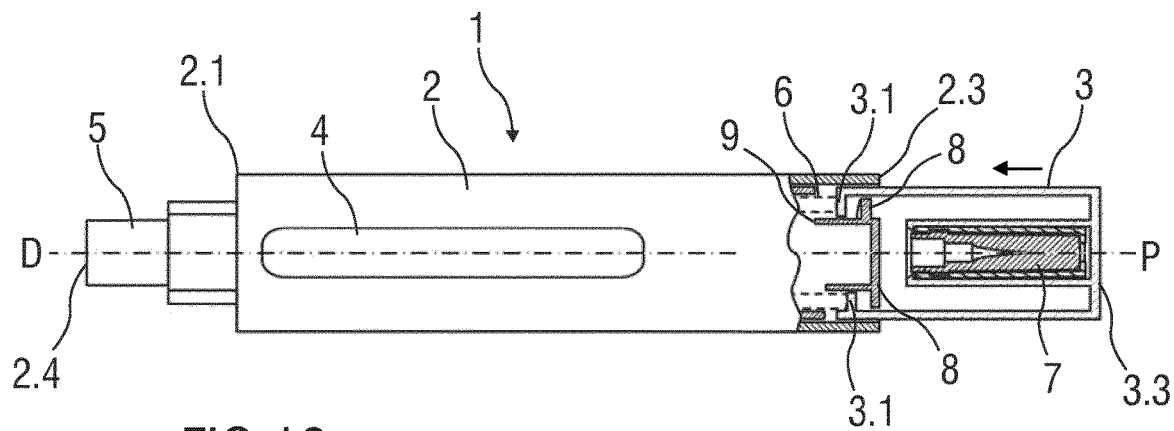
FIG 10

DRUG DELIVERY DEVICE

CROSS REFERENCE TO RELATED APPLICATIONS

The present application is the national stage entry of International Patent Application No. PCT/EP2017/067503, filed on Jul. 12, 2017, and claims priority to Application No. EP 16179488.8, filed on Jul. 14, 2016, the disclosures of which are incorporated herein by reference.

TECHNICAL FIELD

The present disclosure generally relates to a drug delivery device.

BACKGROUND

Administering an injection is a process which presents a number of risks and challenges for users and healthcare professionals, both mental and physical. Pre-filled syringes containing a selected dosage of a medicament for administering the medicament to a patient are known in the art.

There remains a need for an improved drug delivery device.

SUMMARY

An object of the present disclosure is to provide an improved drug delivery device.

The object is achieved by a drug delivery device according to claim 1.

Exemplary embodiments are provided in the dependent claims.

According to the present disclosure, a drug delivery device includes:
- a body adapted to retain a medicament cartridge,
- a cap attachable to a distal end of the body to cover an opening thereof,
- an activation mechanism arranged within the body, wherein the cap includes an activation feature adapted to be inserted into an activation opening of the body in order to actuate the activation mechanism or allow actuation thereof.

Actuation of the activating mechanism may be the only requirement or one out of a number of requirements to initiate a drug dispense operation of the drug delivery device. According to the present disclosure, the cap, which is otherwise used to cover the opening of the body, through which the drug is dispensed and prevent access to an injection needle which may be present in this opening, is also used to actuate the activating mechanism. The cap may thus serve as a trigger button or as a key to unlock the activating mechanism allowing operation of a different trigger button or sleeve to start the drug dispense operation. Patients using the drug delivery device are thus provided with an additional safety measure in order to avoid accidental triggering of the drug delivery device.

In an exemplary embodiment the activation feature is arranged on a proximal end of the cap or on a distal end of the cap or on a lateral face thereof.

In an exemplary embodiment the activation opening is arranged in a proximal end of the body or in a lateral face of the body.

In an exemplary embodiment the cap includes an activation feature in the form of a sheath grabber within the cap for engaging a protective needle sheath.

In an exemplary embodiment the activation feature has the form of one or more activation ribs adapted to be inserted into activation openings having the form of lateral notches within the proximal end of the body in order to actuate the activation mechanism.

In an exemplary embodiment the activation feature includes one or more inwardly directed ribs within the cap adapted to engage an outer thread arranged within the proximal end of the body allowing the cap to be screwed into the proximal end.

In order to avoid accidental activation, an insertion movement of the activation feature into the activation opening may be decoupled from an actuation movement of the cap.

In an exemplary embodiment, when the cap has been screwed into the proximal end, the activation feature engages the activation mechanism such that the cap may be depressed in the distal direction in order to actuate the activation mechanism. This is one possible way to decouple the insertion movement of the activation feature from the actuation movement of the cap thus reducing the risk of accidental actuation.

In an exemplary embodiment the activation feature has the form of a key suitable for transmitting a torque, e.g. a hexalobular external key in order to allow for actuating the activation mechanism by rotating the cap. This is another possible way to decouple the insertion movement of the activation feature from the actuation movement of the cap thus reducing the risk of accidental actuation.

In an exemplary embodiment the cap includes a grip feature adapted to facilitate gripping the cap by a user's hand and/or fingers. In particular, the grip feature may includes one or more extensions in a transversal direction. This may facilitate removal of the cap from the distal end if the body and rotational movement of the cap for insertion or actuation. The grip feature may be reusable and/or tailored to the hand or fingers of an individual user.

In an exemplary embodiment the cap is adapted to be placed laterally on the body for engaging the actuation feature to the actuation mechanism such that an end of the cap is substantially flush with the distal end of the body to render the drug delivery device more manageable and/or to increase a supporting surface of the drug delivery device 1 on an injection site, e.g. a patient's skin.

In an exemplary embodiment, a sleeve is telescoped within the distal end of the body, wherein the sleeve is adapted to be moved in the proximal direction relative to the body in order to expose the injection needle and/or to actuate the drug delivery device and/or to allow actuation of the activation mechanism.

In an exemplary embodiment, the sleeve is interlocked to the activation mechanism, e.g. such that the activation mechanism is locked prior to depression of the sleeve, wherein the sleeve has to be depressed in the proximal direction in order to unlock the activation mechanism which can only then be operated by the activation feature on the cap in order to dispense the drug. In another exemplary embodiment, the interlock may be such that sleeve is locked prior to operation of the activation mechanism, wherein the activation feature on the cap has to operate the activation mechanism in order to unlock the sleeve, wherein subsequent depression of the sleeve in the proximal direction activates the drug delivery device in order to dispense the drug. In yet another exemplary embodiment, it may be required to depress the sleeve and to operate the activation mechanism by the activation feature of the cap to dispense the drug without having to observe a sequence of operation.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become more fully understood from the detailed description given below and the accompanying drawings, which are given by way of illustration only, and do not limit the present disclosure, and wherein:

FIG. 7 is a schematic longitudinal section of an exemplary embodiment of a cap having activation ribs for actuating an activation mechanism of a drug delivery device, FIG. 8 is a schematic view of a proximal face of the cap of FIG. 7, FIG. 9 is a schematic view of an exemplary embodiment of a drug delivery device including a body and a cap after removal of the cap and prior to assembly of the cap to the proximal end of the body, FIG. 10 is a schematic view of an exemplary embodiment of a drug delivery device after removal of a cap and during assembly of the cap to the proximal end thereof for actuating an activation mechanism of the drug delivery device.

Corresponding parts are marked with the same reference symbols in all figures.

DETAILED DESCRIPTION

Figure 1:
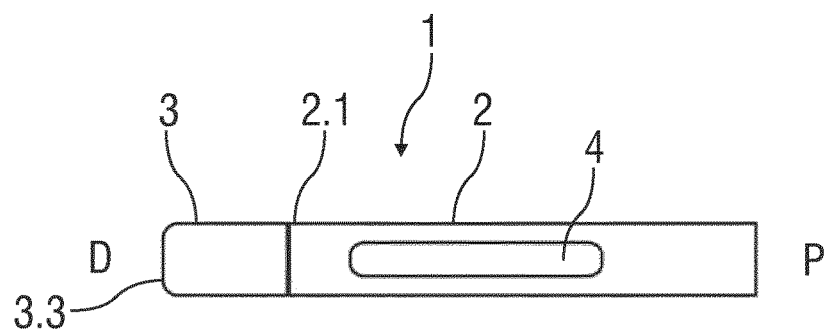
FIG. 1 is a schematic view of an exemplary embodiment of a drug delivery device including a body and a cap attached to a distal end thereof.

FIG. 1 is a schematic view of an exemplary embodiment of a drug delivery device 1 including a body 2 and a cap 3 attached to a distal end 2.1 of the body 2. The body 2 may be adapted to retain a medicament cartridge to which an injection needle may be attached or a medicament cartridge in the form of a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. The body 2 may include a viewing window 4 allowing inspection of the contents of the medicament cartridge or syringe. An activation mechanism may be arranged within the body 2, the activation mechanism adapted to advance the syringe and needle and/or to advance a stopper within the syringe for displacing a drug contained in the syringe through the injection needle.

Figure 2:
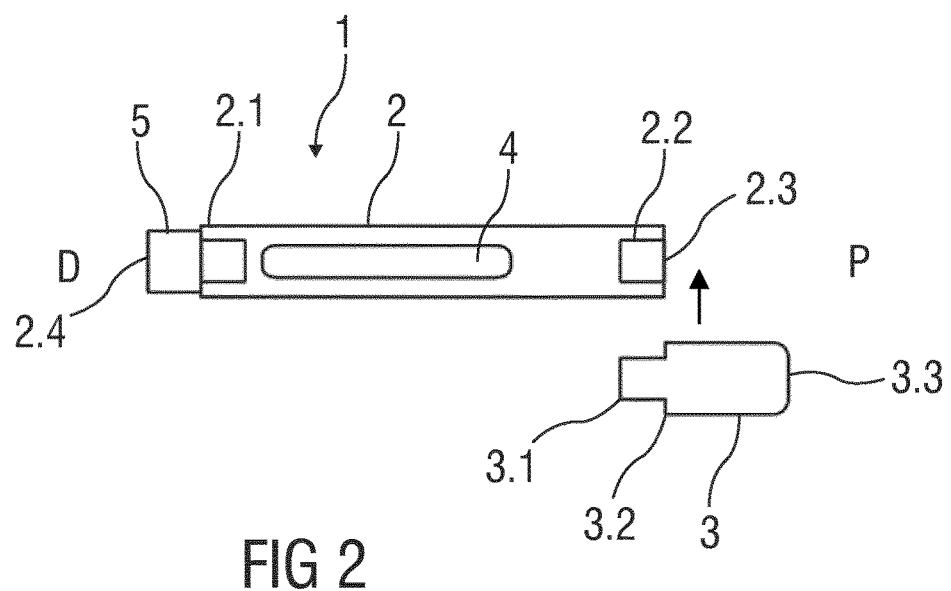
FIG. 2 is a schematic view of the drug delivery device after removal of the cap.

FIG. 2 is a schematic view of the drug delivery device 1 after removal of the cap 3 from the distal end 2.1 of the body 2. In the exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device 1 and/or to allow actuation of the activation mechanism. The cap 3 includes an activation feature 3.1 having the form of an attachment intended to be inserted into an activation opening 2.2 of the body 2 in order to actuate the activation mechanism or in order to allow movement of the sleeve 5 for actuating the drug delivery device 1. FIG. 2 shows the cap 3 reversed with respect to its orientation in FIG. 1, i.e. a distal end 3.3 of the cap 3 points in the proximal direction P of the drug delivery device 1. In this embodiment, the activation feature 3.1 is arranged on a proximal end 3.2 of the cap 3. The man skilled in the art will readily understand that the activation feature 3.1 may likewise be arranged on a distal end 3.3 of the cap 3 or on a lateral face thereof. In the embodiment of FIG. 2, the activation opening 2.2 of the body 2 into which the activation feature 3.1 may be inserted is arranged in a proximal end 2.3 of the body 2. The man skilled in the art will readily understand that the activation opening 2.2 may likewise be arranged in a lateral face of the body 2. The insertion movement may be a movement of the cap 3 in the distal direction D or in a radial direction towards the body 2. In an exemplary embodiment, the cap 3 may be inserted into the activation opening 2.2 in the radial direction to engage but not yet actuate the activation mechanism. The user may then have to depress the cap 3 in the distal direction D to actuate the activation mechanism.

Figure 3:
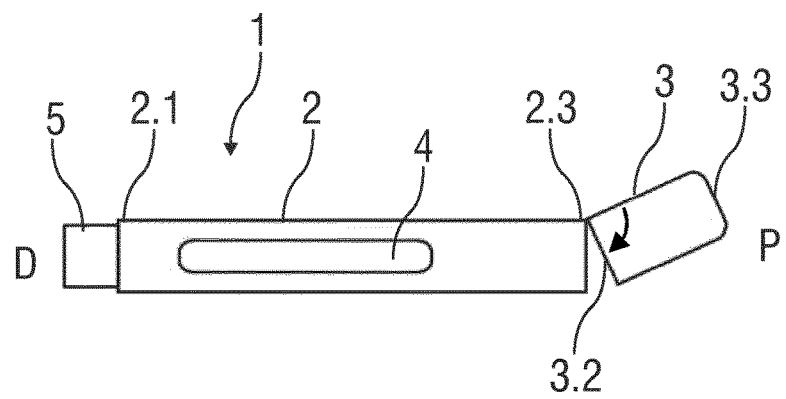
FIG. 3 is a schematic view of the drug delivery device while the cap is being attached to a proximal end of the body.

FIG. 3 is a schematic view of the drug delivery device 1 while the cap 3 is being attached to a proximal end 2.3 of the body 2. In this embodiment, the cap 3 may be hinged to the proximal end 2.3 of the body 2 and rotated into position in order to actuate the activation mechanism or in order to allow movement of the sleeve 5 for actuating the drug delivery device 1. For this purpose, the cap 3 may be hooked into a hinge at the proximal end 2.3 of the body 2 after having been removed from the distal end 2.1 thereof.

Figure 4:
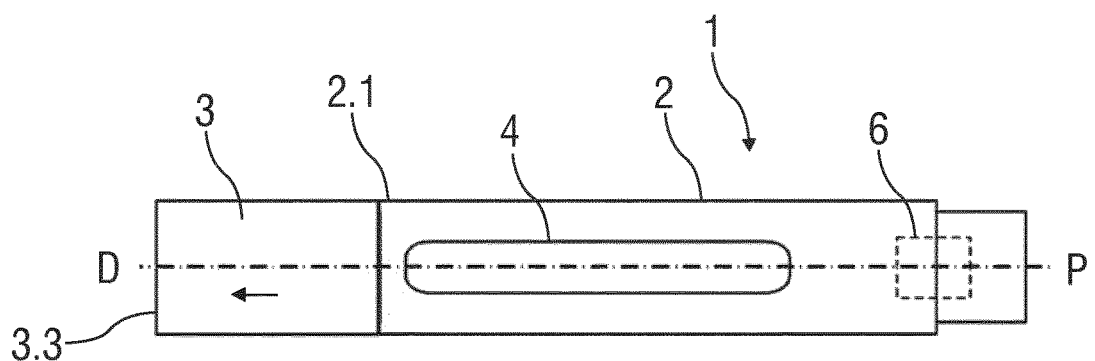
FIG. 4 is a schematic view of an exemplary embodiment of a drug delivery device including a body and a cap attached to a distal end thereof.

FIG. 4 is a schematic view of an exemplary embodiment of a drug delivery device 1 including a body 2 and a cap 3 attached to a distal end 2.1 of the body 2. The body 2 may be adapted to retain a medicament cartridge to which an injection needle may be attached or a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. The body 2 may include a viewing window 4 allowing inspection of the contents of the medicament cartridge or syringe. An activation mechanism 6 may be arranged within the body 2, the activation mechanism 6 adapted to advance the syringe and needle and/or to advance a stopper within the syringe for displacing a drug contained in the syringe through the injection needle when operated by the activation feature 3.1 of the cap 3.

Figure 5:
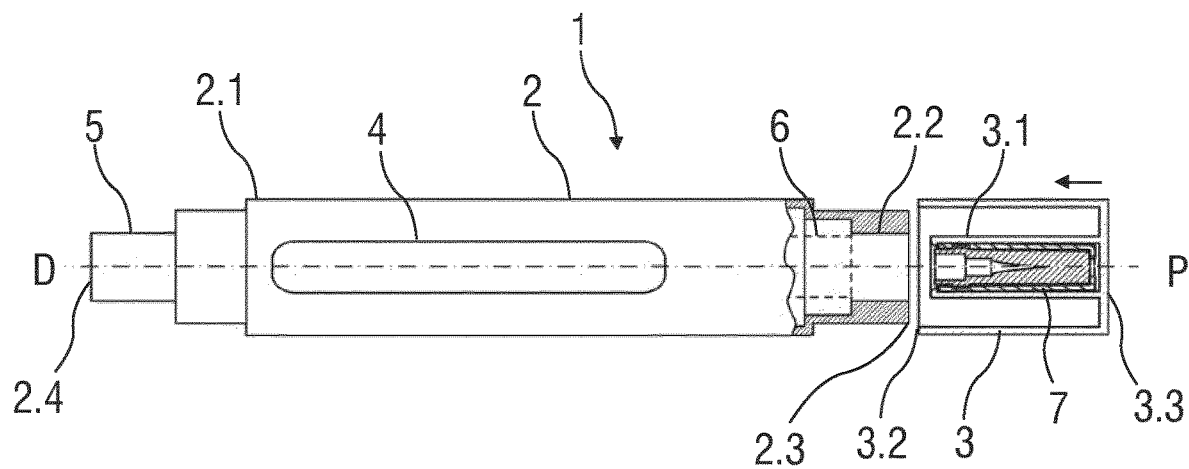
FIG. 5 is a schematic view of the drug delivery device after removal of the cap and during assembly of the cap to the proximal end of the body.

FIG. 5 is a schematic view of the drug delivery device 1 after removal of the cap 3 and during assembly of the cap 3 to the proximal end 2.3 of the body 2. In the exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device 1 after the activation mechanism 6 has been actuated and/or to allow actuation of the activation mechanism 6. The cap 3 includes an activation feature 3.1 in the form of a sheath grabber within the cap 3 for engaging a protective needle sheath 7. The cap 3 is adapted to be reversed and placed over the proximal end 2.3 of the body 2, wherein the activation feature 3.1 is inserted into an activation opening 2.2 in the proximal end 2.3 of the body 2 in order to actuate the activation mechanism 6 or in order to allow movement of the sleeve 5 for actuating the activation mechanism 6. FIG. 5 shows the cap 3 reversed with respect to its orientation in FIG. 4, i.e. a distal end 3.3 of the cap 3 points in the proximal direction P of the drug delivery device 1. In this embodiment, the activation feature 3.1 is arranged within the cap 3 and points towards a proximal end 3.2 of the cap 3. In the embodiment of FIG. 5, the activation opening 2.2 of the body 2 into which the activation feature 3.1 may be inserted is arranged in a proximal end 2.3 of the body 2. The man skilled in the art will readily understand that the activation opening 2.2 may likewise be arranged in a lateral face of the body 2.

Figure 6:
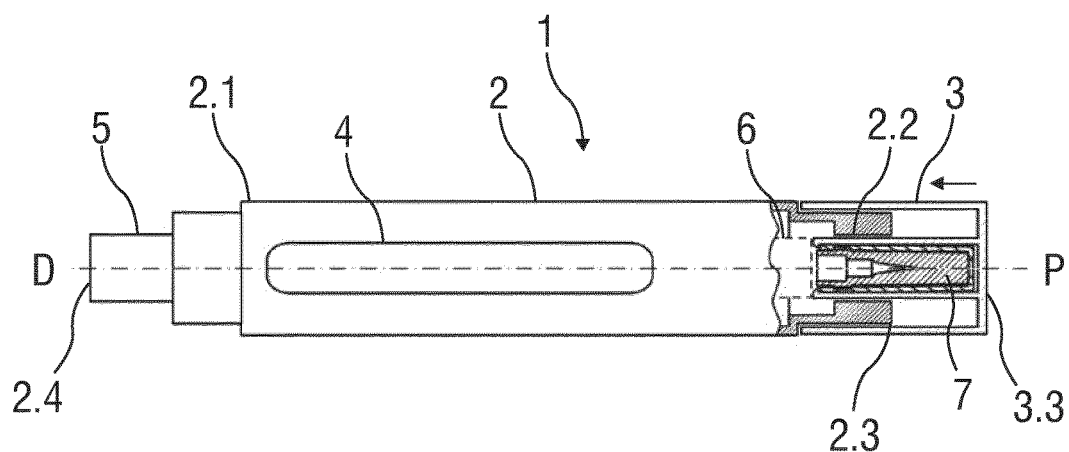
FIG. 6 is a schematic view of the drug delivery device with the cap assembled to the proximal end of the body for actuating an activation mechanism of the drug delivery device.

FIG. 6 is a schematic view of the drug delivery device 1 with the cap 3 assembled to the proximal end 2.3 of the body 2 for actuating the activation mechanism 6 of the drug delivery device 1. The cap 3 has been fully pushed on the proximal end 2.3 and the activation feature 3.1 has thus engaged the activation mechanism 6 and displaced it in the distal direction D.

FIG. 7 is a schematic longitudinal section of an exemplary embodiment of a cap 3 having an activation feature 3.1 in the form of activation ribs for actuating an activation mechanism 6 of a drug delivery device 1 similar to the one shown in FIGS. 4 to 6. FIG. 8 is a schematic view of a proximal end 3.2 of the cap 3 of FIG. 7. The cap 3 is adapted to be reversed and placed over the proximal end 2.3 of the body 2, wherein the one or more activation features 3.1 are inserted e.g. into lateral notches within the proximal end 2.3 of the body 2 in order to actuate the activation mechanism 6 or in order to allow movement of the sleeve 5 for actuating the drug delivery device 1.

FIG. 9 is a schematic view of an exemplary embodiment of a drug delivery device 1 including a body 2 and a cap 3 after removal of the cap 3 and prior to assembly of the cap 3 to the proximal end 2.3 of the body 2. In the exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device 1 after the activation mechanism 6 has been actuated and/or to allow actuation of the activation mechanism 6. The cap 3 includes an activation feature 3.1 in the form of one or more inwardly directed ribs within the cap 3 adapted to engage an outer thread 8 arranged within the proximal end 2.3 of the body 2. The outer thread 8 may be arranged on casework 9 within the body 2 which may be fixed relative to the body 2. The cap 3 is adapted to be reversed and screwed into the proximal end 2.3 of the body 2, wherein the activation feature 3.1 is inserted into an activation opening 2.2 in the proximal end 2.3 of the body 2 in order to actuate the activation mechanism 6 or in order to allow movement of the sleeve 5 for actuating the drug delivery device 1. FIG. 9 shows the cap 3 reversed with respect to its orientation when attached to the distal end 2.1 of the body 2, i.e. a distal end 3.3 of the cap 3 points in the proximal direction P of the drug delivery device 1. In the illustrated embodiment the activation opening 2.2 of the body 2 into which the activation feature 3.1 may be inserted is arranged in a proximal end 2.3 of the body 2. The man skilled in the art will readily understand that the activation opening 2.2 may likewise be arranged in a lateral face of the body 2.

FIG. 10 is a schematic view of the drug delivery device 1 with the cap 3 screwed into the proximal end 2.3 of the body 2 for actuating the activation mechanism 6 of the drug delivery device 1. The cap 3 has been screwed into the proximal end 2.3 and the activation feature 3.1 has thus engaged the activation mechanism 6. In a next step, the cap 3 may be pressed in the distal direction D in order to actuate and displace the activation mechanism 6 in the distal direction D in order to actuate the drug delivery device 1 or in order to allow movement of the sleeve 5 for actuating the drug delivery device 1.

Figure 11:
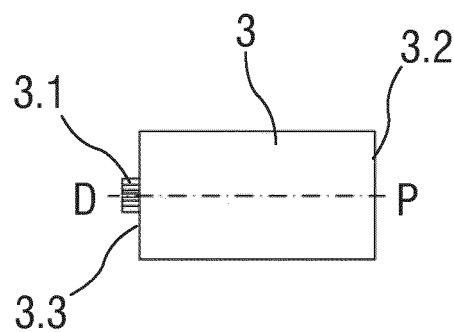
FIG. 11 is a schematic longitudinal section of an exemplary embodiment of a cap having a key for actuating an activation mechanism of a drug delivery device.
Figure 12:
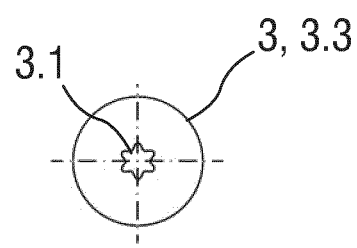
FIG. 12 is a schematic view of a distal face of the cap of FIG. 11.

FIG. 11 is a schematic longitudinal section of an exemplary embodiment of a cap 3 having an activation feature 3.1 in the form of a key for actuating an activation mechanism 6 of a drug delivery device 1. FIG. 12 is a schematic view of a distal end 3.3 or distal face of the cap 3 of FIG. 11. In this embodiment, the activation feature 3.1 is arranged on the distal end 3.3 of the cap 3. The man skilled in the art will readily understand that the activation feature 3.1 may likewise be arranged on a lateral face of the cap 3. In the illustrated embodiment the activation feature 3.1 has the form of a six point star shape or hexalobular external key. The man skilled in the art will readily understand that the activation feature 3.1 may also have any other form suitable for transmitting a torque.

Figure 13:
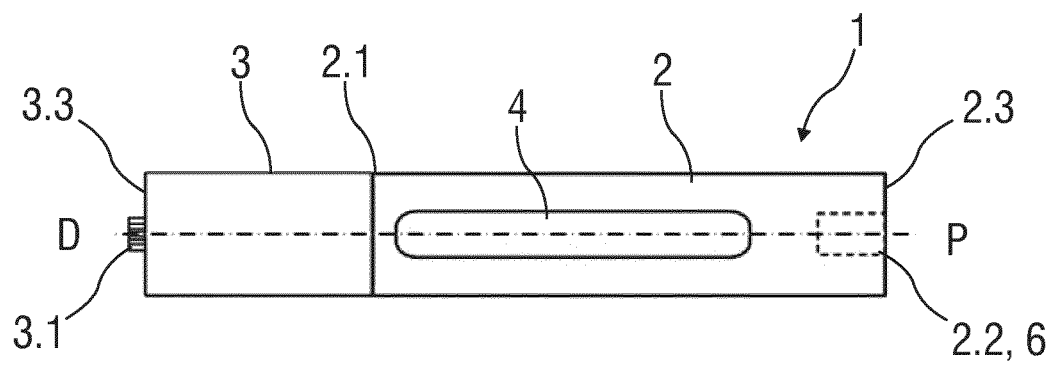
FIG. 13 is a schematic view of an exemplary embodiment of a drug delivery device including a body and the cap of FIGS. 11 and 12 attached to the distal end thereof.

FIG. 13 is a schematic view of an exemplary embodiment of a drug delivery device 1 including a body 2 and the cap 3 of FIGS. 11 and 12 attached to the distal end 2.1 of the body 2. The body 2 may be adapted to retain a medicament cartridge to which an injection needle may be attached or a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. The body 2 may include a viewing window 4 allowing inspection of the contents of the medicament cartridge or syringe. An activation mechanism 6 may be arranged within the body 2, the activation mechanism 6 adapted to advance the syringe and needle and/or to advance a stopper within the syringe for displacing a drug contained in the syringe through the injection needle.

Figure 14:
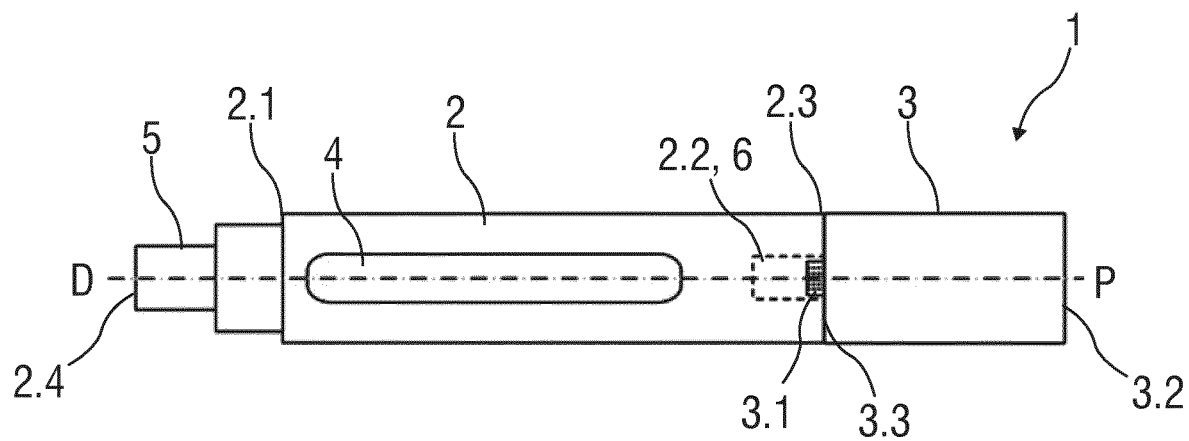
FIG. 14 is a schematic view of the drug delivery device with the cap removed from the distal end and attached to the proximal end of the body for actuating an activation mechanism of the drug delivery device.

FIG. 14 is a schematic view of the drug delivery device 1 after removal of the cap 3 and during application of the cap 3 to the proximal end 2.3 of the body 2. In the exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device 1 after the actuation mechanism 6 has been actuated and/or to allow actuation of the activation mechanism 6. The cap 3 is adapted to be applied to the proximal end 2.3 of the body 2 without being reversed, wherein the activation feature 3.1 is inserted into an activation opening 2.2 in the proximal end 2.3 of the body 2 in order to actuate the activation mechanism 6, e.g. by rotating it. FIG. 14 shows the cap 3 having the same orientation as in FIGS. 11 and 13, i.e. a distal end 3.3 of the cap 3 points in the distal direction D of the drug delivery device 1. In the embodiment of FIGS. 13, and 14, the activation opening 2.2 of the body 2 into which the activation feature 3.1 may be inserted is arranged in a proximal end 2.3 of the body 2. The man skilled in the art will readily understand that the activation opening 2.2 may likewise be arranged in a lateral face of the body 2.

Figure 15:
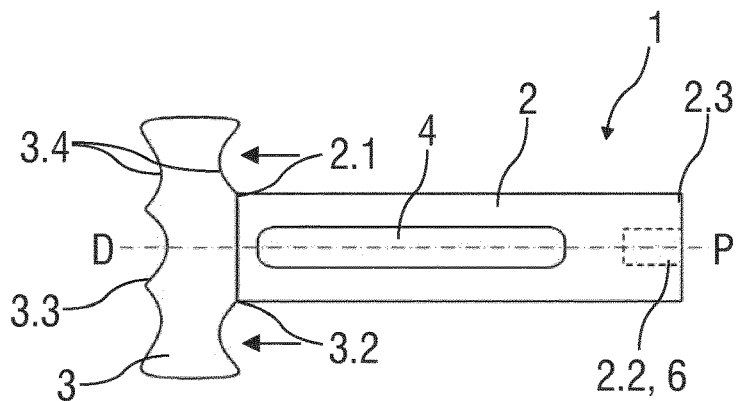
FIG. 15 is a schematic view of an exemplary embodiment of a drug delivery device including a body and a cap attached to a distal end thereof.

FIG. 15 is a schematic view of an exemplary embodiment of a drug delivery device 1 including a body 2 and a cap 3 attached to a distal end 2.1 of the body 2. The body 2 may be adapted to retain a medicament cartridge to which an injection needle may be attached or a pre-filled syringe with an attached injection needle, which may extend from or be extended through an opening 2.4 in the distal end 2.1 (not illustrated). The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1. In the illustrated embodiment, the cap 3 includes a grip feature 3.4 adapted to facilitate gripping the cap 3 by a user's hand and/or fingers. The grip feature 3.4 may extend in a transversal direction, i.e. at right angles with respect to a longitudinal direction of the drug delivery device 1. The grip feature 3.4 or the whole cap 3 may be a reusable part. Furthermore, the grip feature 3.4 may be adapted to an individual user's hand.

The body 2 may include a viewing window 4 allowing inspection of the contents of the medicament cartridge or syringe. An activation mechanism 6 may be arranged within the body 2, the activation mechanism 6 adapted to advance the syringe and needle and/or to advance a stopper within the syringe for displacing a drug contained in the syringe through the injection needle.

Figure 16:
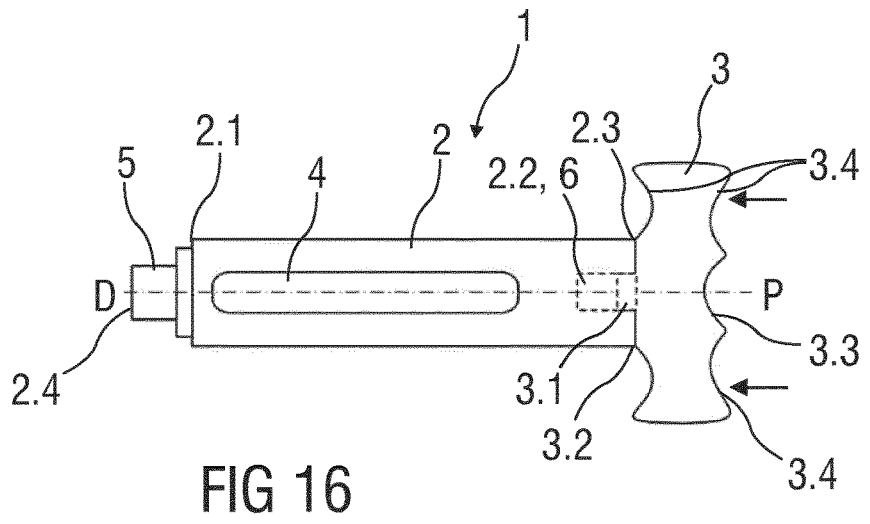
FIG. 16 is a schematic view of the drug delivery device with the cap removed from the distal end and attached to a proximal end thereof for actuating an activation mechanism of the drug delivery device.

FIG. 16 is a schematic view of the drug delivery device 1 after removal of the cap 3 from the distal end 2.1 of the body 2. In the exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device 1 after the actuating mechanism 6 has been actuated and/or to allow actuation of the activation mechanism 6. The cap 3 includes an activation feature 3.1 having the form of an attachment intended to be inserted into an activation opening 2.2 of the body 2 in order to actuate the activation mechanism 6 or in order to allow movement of the sleeve 5 for actuating the drug delivery device 1. FIG. 16 shows the cap 3 reversed with respect to its orientation in FIG. 15, i.e. a distal end 3.3 of the cap 3 points in the proximal direction P of the drug delivery device 1. In this embodiment, the activation feature 3.1 is arranged on a proximal end 3.2 of the cap 3. The man skilled in the art will readily understand that the activation feature 3.1 may likewise be arranged on a distal end 3.3 of the cap 3 or on a lateral face thereof. In the embodiment of FIGS. 15 and 16, the activation opening 2.2 of the body 2 into which the activation feature 3.1 may be inserted is arranged in a proximal end 2.3 of the body 2. The man skilled in the art will readily understand that the activation opening 2.2 may likewise be arranged in a lateral face of the body 2.

Figure 17:
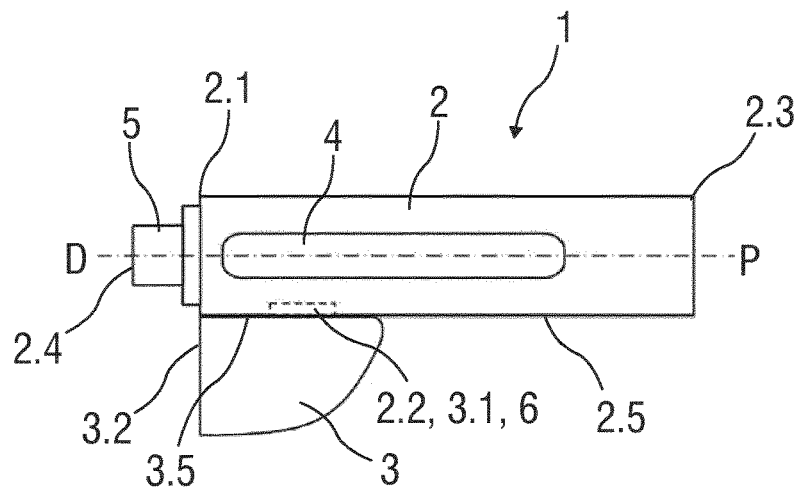
FIG. 17 is a schematic view of an exemplary embodiment of a drug delivery device including a body and a cap adapted to be attached to a distal end thereof, wherein the cap is removed from the distal end and instead attached to the body laterally for actuating an activation mechanism of the drug delivery device.

FIG. 17 is a schematic view of an exemplary embodiment of a drug delivery device 1 including a body 2 and a cap 3 adapted to be attached to a distal 2.1 end of the body 2, wherein in FIG. 17 the cap 3 is removed from the distal end 2.1 and instead attached to the body 2 laterally for actuating an activation mechanism 6 of the drug delivery device 1. The body 2 may be adapted to retain a medicament cartridge to which an injection needle may be attached or a pre-filled syringe with an attached injection needle, which may extend from or be extended through an opening 2.4 in the distal end 2.1. The cap 3 is adapted to cover the opening 2.4 in the distal end 2.1 of the body 2 to prevent access to the injection needle. Furthermore, the cap 3 may be adapted to engage a protective needle sheath arranged over the injection needle in order to remove the protective needle sheath upon removal of the cap 3 from the distal end 2.1.

The body 2 may include a viewing window 4 allowing inspection of the contents of the medicament cartridge or syringe. An activation mechanism 6 may be arranged within the body 2, the activation mechanism 6 adapted to advance the syringe and needle and/or to advance a stopper within the syringe for displacing a drug contained in the syringe through the injection needle.

FIG. 17 shows drug delivery device 1 after removal of the cap 3 from the distal end 2.1 of the body 2. In the exemplary embodiment, a sleeve 5 is telescoped within the distal end 2.1 of the body 2, wherein the sleeve 5 may be adapted to be moved in a proximal direction P into the body 2 in order to expose the injection needle and/or to actuate the drug delivery device 1 after the activation mechanism 6 has been actuated and/or to allow actuation of the activation mechanism 6. The cap 3 includes an activation feature 3.1 having the form of an attachment intended to be inserted into an activation opening 2.2 of the body 2 in order to actuate the activation mechanism 6 or in order to allow movement of the sleeve 5 for actuating the drug delivery device 1. FIG. 17 shows the cap 3 reversed with respect to its orientation when placed of the distal end 2.1 of the body 2, i.e. a distal end 3.3 of the cap 3 points in the proximal direction P of the drug delivery device 1. In this embodiment, the activation feature 3.1 is arranged on a lateral face 3.5 of the cap 3. The man skilled in the art will readily understand that the activation feature 3.1 may likewise be arranged on the distal end 3.3 or on the proximal end 3.2 of the cap 3. In the embodiment of FIG. 17, the activation opening 2.2 of the body 2 into which the activation feature 3.1 may be inserted is arranged on a lateral face 2.5 of the body 2.

In the embodiment of FIG. 17, the cap 3 may be placed laterally on the body 2 such that the proximal end 3.2 of the cap 3 is substantially flush with the distal end 2.1 of the body 2. Thus, the cap 3 serves as an expansion of the body 2 to render the drug delivery device 1 more manageable and/or to increase a supporting surface of the drug delivery device 1 on an injection site, e.g. a patient's skin.

In all above described embodiments, the activation mechanism 6 may include a connecting rod which may be operated by the activation feature 3.1 on the cap 3, wherein the cap 3 is used as a trigger button, wherein actuation of the cap 3, e.g. depression or rotation, moves the connecting rod which in turn displaces the stopper in the syringe or medicament cartridge to dispense the drug. Likewise, in all above described embodiments, the activation mechanism 6 may include an energy source such as a spring, which may be released by actuation of the cap 3, e.g. depression or rotation, in order to allow the energy source to displace the stopper in the syringe or medicament cartridge to dispense the drug.

The above described embodiments respectively include a sleeve 5, which may be interlocked to the activation mechanism 6, e.g. such that the activation mechanism 6 is locked prior to depression of the sleeve 5, wherein the sleeve 5 has to be depressed in the proximal direction P in order to unlock the activation mechanism 6 which can only then be operated by the activation feature 3.1 on the cap 3 in order to dispense the drug. In another exemplary embodiment, the interlock may be such that sleeve 5 is locked prior to operation of the activation mechanism 6, wherein the activation feature 3.1 on the cap 3 has to operate the activation mechanism 6 in order to unlock the sleeve 5, wherein subsequent depression of the sleeve 5 in the proximal direction P activates the drug delivery device 1 in order to dispense the drug. In yet another exemplary embodiment, it may be required to depress the sleeve 5 and to operate the activation mechanism 6 by the activation feature 3.1 of the cap 3 to dispense the drug without having to observe a sequence of operation. In yet another embodiment, any one of the above described and illustrated embodiments may be without the sleeve 5 so that only operation of the activation mechanism 6 by the activation feature 3.1 of the cap 3 results in dispense of the drug. Furthermore, an additional trigger button may be provided, which has to be depressed in order to dispense the drug.

In order to avoid accidental activation, the insertion movement of the activation feature 3.1 into the activation opening 2.2 can be decoupled from an actuation movement of the cap 3 as in some of the above described embodiments, e.g. by inserting through rotation or by insertion in a radial direction and activating by depression in the distal direction D.

The man skilled in the art will readily understand that the features of the embodiments shown in the figures and described above may be combined with each other.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device 1 may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device 1. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices 1 and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin. Exemplary GLP-1, GLP-1 analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not include a full-length antibody polypeptide, but that still includes at least a portion of a full-length antibody polypeptide that is capable of binding to an antigen. Antibody fragments can include a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations including (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 drug delivery device
2 body
2.1 distal end
2.2 activation opening
2.3 proximal end
2.4 opening
2.5 lateral face
3 cap
3.1 activation feature
3.2 proximal end
3.3 distal end
3.4 grip feature
3.5 lateral face
4 viewing window
5 sleeve
6 activation mechanism
7 protective needle sheath
8 outer thread
9 casework
D distal direction
P proximal direction

The invention claimed is:

1. A drug delivery device, comprising:
a body adapted to retain a medicament cartridge;
a cap attachable to a distal end of the body to cover an opening of the body; and
an activation mechanism arranged within the body,
wherein the cap comprises an activation feature adapted to be inserted into an activation opening of the body in order to actuate the activation mechanism or to allow actuation of the activation mechanism,
wherein the activation feature is in a form of a sheath grabber within the cap for engaging a protective needle sheath, and
wherein the activation opening is arranged in a proximal end of the body or in a lateral face of the body.

2. A drug delivery device according to claim 1, wherein the activation feature is arranged on a proximal end of the cap, on a distal end of the cap, or on a lateral face of the cap.

3. A drug delivery device according to claim 1, wherein the body defines a plurality of activation openings in a form of lateral notches within the proximal end of the body for actuating the activation mechanism, and wherein the activation feature comprises one or more activation ribs adapted to be inserted into the plurality of activation openings.

4. A drug delivery device according to claim 1, wherein the activation feature comprises one or more inwardly directed ribs within the cap adapted to engage an outer thread arranged within the proximal end of the body for allowing the cap to be screwed into the proximal end of the body.

5. A drug delivery device according to claim 4, wherein when the cap has been screwed into the proximal end of the body, the activation feature engages the activation mechanism such that the cap can be depressed in a distal direction in order to actuate the activation mechanism.

6. A drug delivery device according to claim 1, wherein the activation feature comprises a key suitable for transmitting a torque.

7. A drug delivery device according to claim 6, wherein the activation feature comprises a hexalobular external key.

8. A drug delivery device according to claim 1, wherein the cap comprises a grip feature adapted to facilitate gripping of the cap by a user's hand and/or fingers.

9. A drug delivery device according to claim 8, wherein the grip feature comprises one or more extensions in a transversal direction.

10. A drug delivery device according to claim 1, wherein the cap is adapted to be placed laterally on the body for engaging the activation feature with the activation mechanism such that an end of the cap is substantially flush with the distal end of the body.

11. A drug delivery device according to claim 1, wherein an insertion movement of the activation feature into the activation opening is decoupled from an actuation movement of the cap.

12. A drug delivery device according to claim 1, wherein a sleeve is telescoped within the distal end of the body.

13. A drug delivery device according to claim 12, wherein the sleeve is adapted to be moved in a proximal direction relative to the body in order to expose an injection needle, and/or to actuate the drug delivery device, and/or to allow actuation of the activation mechanism.

14. A drug delivery device according to claim 13, wherein the sleeve is interlocked to the activation mechanism.

15. A drug delivery device according to claim 1, further comprising the medicament cartridge, the medicament cartridge being retained within the body.

16. A drug delivery device according to claim 15, further comprising an injection needle that is coupled to the medicament cartridge.

17. A drug delivery device, comprising:
a body adapted to retain a medicament cartridge;
a cap attachable to a distal end of the body to cover an opening of the body; and
an activation mechanism arranged within the body,
wherein the cap comprises an activation feature adapted to be inserted into an activation opening of the body in order to actuate the activation mechanism or to allow actuation of the activation mechanism,
wherein the activation opening is arranged in a proximal end of the body or in a lateral face of the body, and
wherein the activation feature comprises a key suitable for transmitting a torque about a longitudinal axis of the drug delivery device.

18. A drug delivery device, comprising:
a body adapted to retain a medicament cartridge;
a cap attachable to a distal end of the body to cover an opening of the body; and
an activation mechanism arranged within the body,
wherein the cap comprises an activation feature adapted to be inserted into an activation opening of the body in order to actuate the activation mechanism or to allow actuation of the activation mechanism,
wherein the activation feature is in a form of a sheath grabber within the cap for engaging a protective needle sheath,
wherein a sleeve is telescoped within the distal end of the body, and
wherein the sleeve is adapted to be moved in a proximal direction relative to the body in order to expose an injection needle, and/or to actuate the drug delivery device, and/or to allow actuation of the activation mechanism.

\* \* \* \* \*